United States Patent [19]

Pesch

[11] Patent Number: 4,696,024
[45] Date of Patent: Sep. 22, 1987

[54] METHOD AND APPARATUS FOR DETECTING FLAWS IN SINGLE CRYSTAL TEST SAMPLES

[75] Inventor: Wilfried Pesch, Munich, Fed. Rep. of Germany

[73] Assignee: MTU Motoren- und Turbinen-Union Muenchen GmbH, Munich, Fed. Rep. of Germany

[21] Appl. No.: 783,453

[22] Filed: Oct. 3, 1985

[30] Foreign Application Priority Data

Oct. 27, 1984 [DE] Fed. Rep. of Germany ....... 3439471

[51] Int. Cl.$^4$ .......................................... G01N 23/207
[52] U.S. Cl. ........................................ 378/73; 378/71; 378/147; 378/150; 378/151; 378/152
[58] Field of Search ...................... 378/70–74, 378/76, 79, 81, 86, 88, 90, 147, 150–154, 160, 901

[56] References Cited

U.S. PATENT DOCUMENTS

| | | | |
|---|---|---|---|
| 3,784,816 | 1/1974 | Abrahamsson | 378/73 |
| 3,852,594 | 12/1974 | Paolini | 378/73 |
| 4,064,437 | 12/1977 | Hirose et al. | 378/73 |
| 4,380,820 | 4/1983 | Cutter | 378/153 |
| 4,404,682 | 9/1983 | Hayashi et al. | 378/72 |
| 4,412,345 | 10/1983 | Workman et al. | 378/81 |
| 4,419,764 | 12/1983 | Kinanen | 378/153 |
| 4,429,411 | 1/1984 | Smither | 378/84 |
| 4,535,469 | 8/1985 | Brandt | 378/81 |
| 4,592,083 | 5/1986 | O'Brien | 378/160 |

FOREIGN PATENT DOCUMENTS

| | | |
|---|---|---|
| 2133972 | 1/1973 | Fed. Rep. of Germany ...... 378/151 |
| 3236109 | 4/1983 | Fed. Rep. of Germany . |
| 0920481 | 4/1982 | U.S.S.R. ............................ 378/72 |

Primary Examiner—Craig E. Church
Assistant Examiner—John C. Freeman
Attorney, Agent, or Firm—W. G. Fasse; D. H. Kane, Jr.

[57] ABSTRACT

A gamma diffractometer is used for examining or testing samples from the materials flaw aspect. More particularly, single crystal blades of turbo engines are inspected by Roentgen radiation and evaluation of reflections with regard to their half peak width and spacings in the profile or curve representing irradiation intensity (I) as a function of a rotational angle ($\alpha$) of a test sample, said spacings representing lattice planes of a plurality of single crystal grains. The half peak widths and the spacings provide an information regarding the presence or absence of material flaws.

4 Claims, 6 Drawing Figures

METHOD AND APPARATUS FOR DETECTING FLAWS IN SINGLE CRYSTAL TEST SAMPLES

FIELD OF THE INVENTION

This invention relates to a method for detecting flaws in single crystal test samples by using radioactive irradiation. The invention also relates to an apparatus for performing the present detecting or testing method.

BACKGROUND OF THE INVENTION

German Patent Publication (DE-OS) No. 3,236,109 discloses, e.g., a method and an apparatus for determining the orientation of a crystal, whereby use is made of the Laue backscatter diagram for displaying the so-called backscatter Roentgen rays which are used to irradiate a crystal. The Laue diagram is well known and does not require further elaboration. In the arrangement of the above publication the X-ray and the detector centerline are oriented at an acute angle relative to the surface of the crystal being tested. The detector output is processed by a computer to determine the angle of the main crystal axes.

The use of the Laue backscatter diagram of Roentgen rays has a disadvantage mainly because flaws in the interior of a test sample, such as a turbine component, cannot be detected. The known method discloses flaws only in the surface zone of the sample to a depth of just a few microns.

OBJECTS OF THE INVENTION

In view of the above it is the aim of the invention to achieve the following objects singly or in combination:

to eliminate the disadvantages inherent in the known method for inspecting single crystal test samples by permitting the inspection of the entire volume of a test sample to ascertain flaws such as imperfections or irregularities in the growth, for example, of a single crystal wherein individual crystallites may cause a diffraction representing such imperfection or irregularity;

to provide a method and an apparatus for implementing the present three-dimensional testing method for providing a display and/or record of the diffraction pattern especially of a single crystal, whereby an evaluation of the diffraction pattern provides information of said imperfections and irregularities; and to perform the inspection quantitatively on the whole or entire test sample, whereby the inspection is entirely automated to preclude subjective influences on the test results.

SUMMARY OF THE INVENTION

According to the present method a single crystal test sample is irradiated with radiation from a gamma source, the intensity profile of a diffracted reflection is picked up by a stationary detector, and the half width of the reflection or diffraction caused amplitude is measured as an indication of the presence of a flaw. The size of the half width also provides information regarding the nature of a flaw. Where several single crystal grains or crystallites cause a flaw, the reflection or diffraction spacing at the lattice planes of the single crystal grains or crystallites is measured for providing information regarding the nature of a flaw including a so-called angle of cut.

The present apparatus for implementing the present method is characterized in that a diffractometer is used including a radioactive gamma source within a shield followed by a collimator, including means for the timed application of a focussed beam to the test sample which is arranged on a turntable associated with a stationary radiation detector and with a control and evaluation device in the form of a central processing unit for causing a display and/or for recording of such flaws as a permanent record for a subsequent evaluation.

The invention has the following advantages. The present method is suitable as a production line inspection method for an automated quality control including final inspections. The inspection is made quantitatively throughout the volume of a test sample and not alone qualitatively in a shallow surface zone. Since the test sample is totally penetrated by radiation, the inspection represents a genuine volume inspection or rather a three-dimensional inspection.

BRIEF DESCRIPTION OF THE DRAWINGS

In order that the invention may be clearly understood, it will now be described, by way of example, with reference to the accompanying drawings, wherein.

Figure 1:
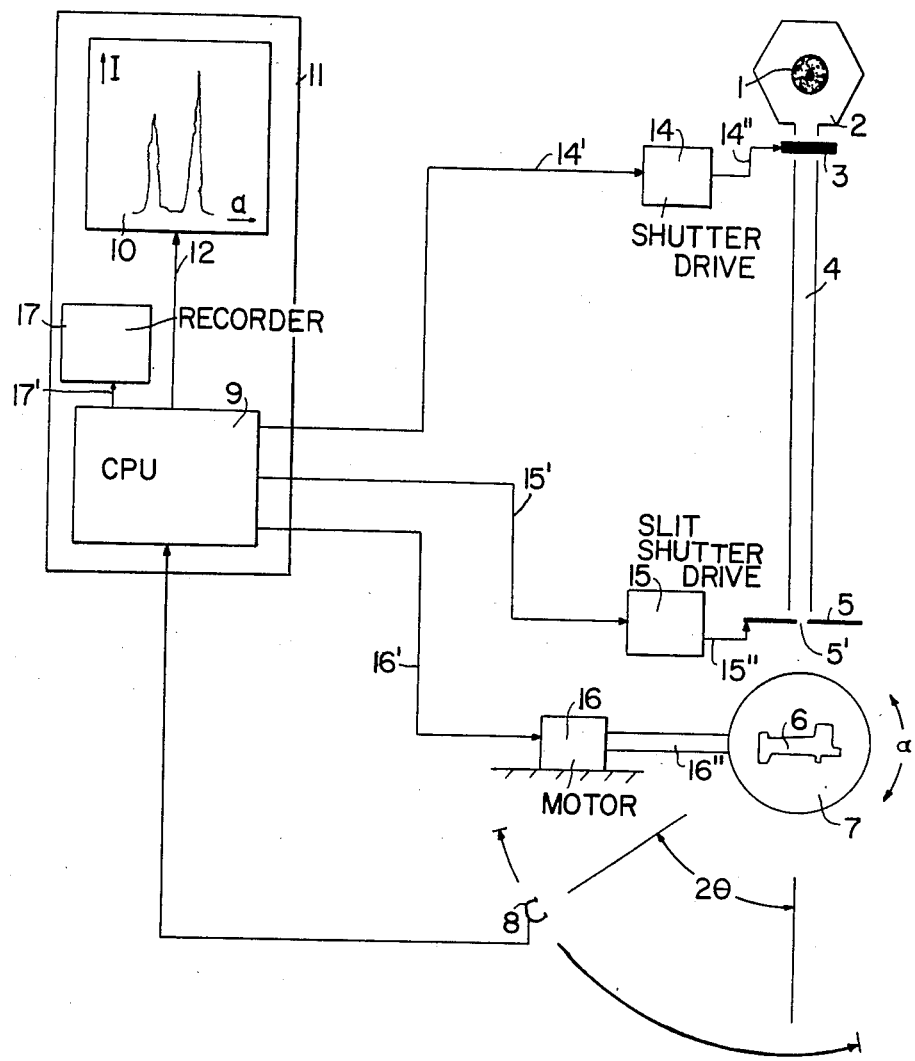
FIG. 1 illustrates an inspection apparatus in the form of a gamma diffractometer according to the invention for performing the present method.

DETAILED DESCRIPTION OF PREFERRED EXAMPLE EMBODIMENTS AND OF THE BEST MODE OF THE INVENTION:

FIG. 1 shows a radioactive source 1 surrounded by a lead shield 2, for radiating gamma rays. A shutter or diaphragm 3 is arranged between an outlet of the lead shield 2 and a collimator 4. The opening and closing of the shutter 3 is controlled by a conventional first shutter drive 14 operatively connected, for example mechanically, to the shutter 3 as shown at 14''. The first shutter drive 14 is connected with its control input 14' to a central processing unit 9 in a housing 11.

The collimator 4 is an elongated tubular member having a length of, for example 4 meters, for focussing the gamma rays. A second shutter or slot diaphragm 5 with a slot 5' is provided at the output end of the collimator 4. The slot 5' can be opened and closed in a predetermined, timed sequence under the control of the central processing unit 9 which controls and operates the diaphragm 5 operatively connected at 15'' to the slit shutter drive 15 which is connected with its control input 15' to the central processing unit 9 for opening and closing the slot 5' in synchronism with the operation of the first shutter 3, whereby the gamma rays pass through the slot 5' onto and through a test sample, such as a turbine blade 6 or 6'.

The central processing unit 9 also operates a display device including a display screen 10 and a recorder 17. The control input 12 of the display device is connected to the central processing unit 9 and so is the control input 17' of the recorder 17.

These components 10 and 16 are of conventional construction. For example the screen can be a cathode ray tube and the recorder can be a graph recorder or so-called plotter.

The sample 6 is arranged on a turntable 7 rotating through an angle $\alpha$. The angle of diffraction $\theta$ is sensed by a stationary detector 8. The signals from the detector 8, especially the relative radiation intensity reading I, measured for example in counts per sec. ($S^{-1}$), are processed and evaluated in the central processing unit 9. The central processing unit 9 controls a turntable drive motor 16, for example a stepping motor, operatively connected at 16" to the turntable 7 carrying the sample 6. The control input 16' of the stepping motor 16 is connected to the central processing unit 9 which drives the stepping motor 16 in synchronism with the two drives 14 and 15. The plotter 17 plots the intensity I as a function of the rotational angle $\alpha$ of the turntable 7.

Figure 2:
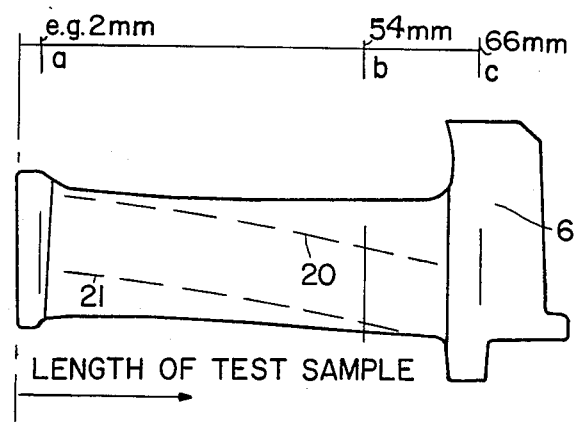
FIG. 2 illustrates a first single crystal turbine blade inspected in accordance with the present method in three predetermined inspection planes.
Figure 3:
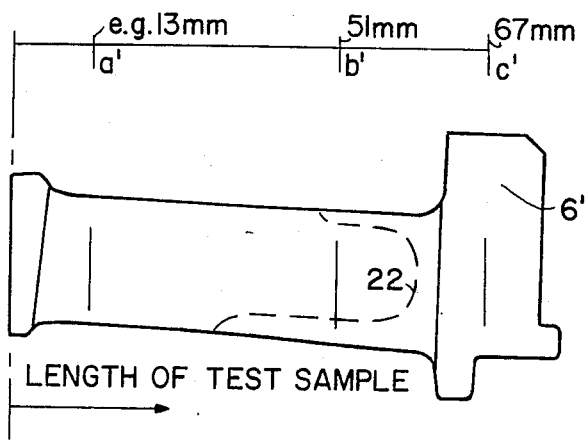
FIG. 3 illustrates a second single crystal blade inspected in accordance with the present method in three predetermined inspection planes which differ from those in FIG. 2.

Diffraction naturally occurs only in the presence of tilted grain "Verkippung" in a crystal. In other words, the results of the inspection are a measure of the purity of the single crystal sample, or the quality of the single crystal growing process. Two tilted grain boundaries 20 and 21 are indicated by dashed lines in the sample 6 of FIG. 2 representing a faulty crystal growth. The samples 6, 6' are placed on the turntable 7 in such fixed positions that predetermined inspection planes a, b, and c will be irradiated by the beam of gamma rays. Inspection plane "a" in FIG. 2 is, for example, spaced 2 mm from the left end of the sample 6, whereas in FIG. 3 it is spaced 13 mm from the left end of sample 6'. Inspection plane "b" is spaced 54 mm in FIG. 2 and 51 mm in FIG. 3. Inspection plane "c" is spaced 66 mm in FIG. 2 and 67 mm in FIG. 3. Selection of the inspection plane will, for example, depend on the shape of the sample and on the primary stress zones of the sample.

Figure 2A:
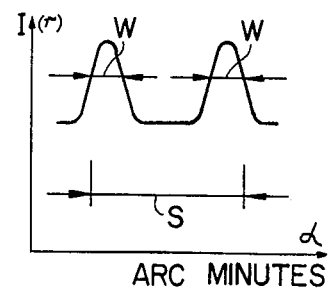
FIG. 2a illustrates the signals including the reflection spacing recorded as a result of inspecting the blade of FIG. 2 exhibiting a flawed crystal growth, whereby only the signals for the third plane are shown since the signals for the first and second inspection planes are similar to those of the third plane.
Figure 3A:
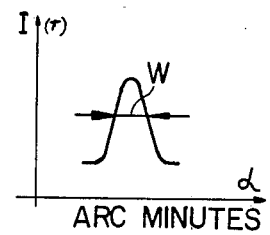
FIG. 3a illustrates a sample of the signals recorded for each inspection plane as a result of inspecting the blade of FIG. 3 exhibiting a normal crystal growth.
Figure 4:
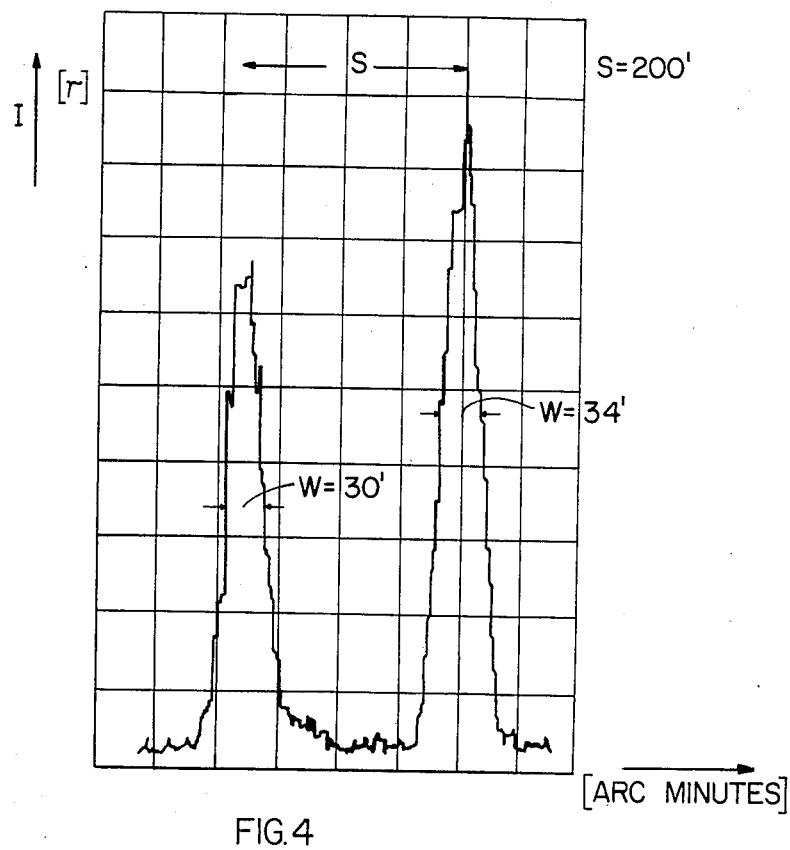
FIG. 4 illustrates a typical inspection log of the inspection of a single crystal test sample by means of a gamma diffractometer as taught herein and showing a so-called "Verkippung" similar to the illustration of FIG. 2a, of the grain boundaries between two neighboring grains in a test sample as shown in FIG. 2.

In FIG. 2, the half peak value W for an actually tested turbine blade for plane "a" was 27' and 24' at the first and second grain boundaries 20 and 21, in plane "b" these values were 26' in both instances, and in plane "c" these values were 34' and 30' as also shown in FIG. 4. The respective reflection spacings S were 173' for plane "a", 186' for plane "b", and 200' for plane "c" also as shown in FIG. 4. FIG. 2a shows the reflection spacing S only once as a representative illustration. This spacing S is taken from peak to peak or from the leading edge of the first amplitude to the trailing of the second amplitude at the half peak value level. The respective values W and S are measured in arc minutes plated along the abscissa in FIGS. 2a, 3a, and 4.

The rotation $\alpha$ of the turntable 7 is also measured in arc minutes, whereby the "cutting" width $\Delta\alpha$ of the inspection planes "a", "b""c" corresponds to 1' as determined by the rotational speed of the turntable 7 and by the opening duration of the slot 5'. Both, the rotational speed or stepping speed of the turntable 7 and the opening duration are determined by the central processing unit 9 in accordance with the respective programming stored in the central processing unit 9.

One or several samples can be inspected with the aid of a gamma diffractometer in a matter of several minutes up to about ½ hour. The half peak width readings here are a measure of the quality of the crystallites and the reflection spacing S in a certain crystal plane corresponds to, or represents the tilting between two grains, whereby conclusions regarding the quality and purity of the crystal growth may be made.

The embodiment of the present invention as here illustrated and described may be varied without departing from the basic teaching. More particularly, the inventive concept also embraces alternative measuring devices for inspection by passing gamma radiation through a test sample. Using other types of relative movement between the turntable and sample on the one hand and the detector on the other hand, than shown in FIG. 1 may be used so long as the spatial distribution of the radiation intensity (2 $\theta$-profile) can be determined. The planes in which the source of radiation and the detector are installed must not necessarily be the same as long as a plurality of measurements allow the determination of one radiation projection based on radiation passing through the test sample.

All components of FIG. 1, including the radiation detector 8 and the central processing unit 9 are, as such, of conventional construction.

Incidentally, $\theta$ is Bragg's diffraction angle. If the radiation emitted by the source 1 has a wave length $\lambda$, the respective equation is as follows $\lambda = 2d \sin \theta$, wherein "d" is the spacing between two neighboring lattice planes.

Although the invention has been described with reference to specific example embodiments, it will be appreciated that it is intended to cover all modifications and equivalents within the scope of the appended claims.

What I claim is:

1. An apparatus for inspecting single crystal test samples for flaws, comprising a radioactive source of gamma rays for passing gamma rays through said test sample, collimator means operatively connected to said source of gamma rays for providing a focussed beam of gamma rays, shutter means arranged for cooperation with said collimator means for controlling a timed application of said focussed beam to a test sample, movement means for providing a relative movement between said source of gamma rays and said test sample so that the test sample is exposed to said focussed beam, stationary detector means located relative to said movement means for detecting an intensity profile of a diffracted reflection of said focussed beam of gamma rays which pass through said sample, and a central processing unit including measuring means operatively connected to said detector means for measuring the half peak width of said reflection as an indication of a flaw in said test sample, wherein said collimator means comprise a tubular collimator for focussing said gamma rays, said shutter means comprising a first shutter located at one end of said tubular collimator facing said source of gamma rays, and a second shutter in the form of a slit stop at an opposite end of said tubular collimator, first drive means (14) for operating said first shutter, second drive means (15) for operating said second shutter, means connecting said first and second drive means also to said central processing unit for controlling the timed application of said focussed beam to a test sample in synchronism with said movement means for detecting an intensity profile of a diffracted reflection throughout the volume of said test sample.

2. The apparatus of claim 1 wherein said movement means comprise a turntable for supporting said test sample, turntable drive means for stepping said turntable, and means connecting said turntable drive means to said central processing unit for stepping said turntable through a test cycle.

3. The apparatus of claim 2, wherein said central processing unit comprises means for displaying and/or recording a detected radiation intensity as a function of a rotational angle of said turntable.

4. The apparatus of claim 1, further comprising means for measuring reflection spacings between lattice planes of a plurality of single crystal grains for ascertaining the purity or quality of the single crystal grains.

* * * * *